US006575937B2

United States Patent
Hansen

(10) Patent No.: US 6,575,937 B2
(45) Date of Patent: Jun. 10, 2003

(54) INFLATION DEVICE WITH STORAGE CHAMBER

(75) Inventor: James G. Hansen, Coon Rapids, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 91 days.

(21) Appl. No.: 09/731,524

(22) Filed: Dec. 6, 2000

(65) Prior Publication Data

US 2002/0068906 A1 Jun. 6, 2002

(51) Int. Cl.[7] .................................................. A61M 5/00
(52) U.S. Cl. ...................................................... 604/181
(58) Field of Search ................................ 604/9, 99, 97, 604/181, 99.02; 128/203.15; 137/556; 206/213.1; 606/108

(56) References Cited

U.S. PATENT DOCUMENTS

| 4,573,977 | A | | 3/1986 | Crawford | 604/212 |
|---|---|---|---|---|---|
| 4,789,000 | A | * | 12/1988 | Aslanian | 137/556 |
| 4,793,351 | A | | 12/1988 | Landman et al. | 128/344 |
| 4,795,431 | A | | 1/1989 | Walling | 604/97 |
| 4,865,587 | A | | 9/1989 | Walling | 604/97 |
| 5,147,300 | A | | 9/1992 | Robinson et al. | 604/97 |
| 5,224,933 | A | | 7/1993 | Bromander | 604/99 |
| 5,334,153 | A | * | 8/1994 | McIntyre et al. | 604/99 |
| 5,740,792 | A | * | 4/1998 | Ashley et al. | 128/203.15 |
| 5,785,685 | A | | 7/1998 | Kugler et al. | 604/96 |
| 5,855,546 | A | | 1/1999 | Hastings et al. | 600/3 |
| 5,976,106 | A | | 11/1999 | Verin et al. | 604/96 |
| 6,036,697 | A | | 3/2000 | DiCaprio | 606/108 |
| 6,050,972 | A | * | 4/2000 | Zadno-Azizi et al. | 604/97 |
| 6,073,759 | A | * | 6/2000 | Lamborne et al. | 206/213.1 |
| 6,090,062 | A | * | 7/2000 | Sood et al. | 604/9 |
| 6,102,931 | A | | 8/2000 | Thornton | 606/194 |
| 6,325,778 | B1 | * | 12/2001 | Zadno-Azizi et al. | 604/99.02 |

OTHER PUBLICATIONS

U.S. patent application Ser. No. 09/644,754, Urick et al., filed Aug. 23, 2000.

* cited by examiner

Primary Examiner—Henry Bennett
(74) Attorney, Agent, or Firm—Crompton, Seager & Tufte, LLC

(57) ABSTRACT

Inflation devices for use with balloon catheters. The inflation devices are preloaded with a fluid stored in a chamber in the plunger. An inflation device in accordance with one embodiment of the present invention includes a barrel defining a primary chamber therein, a plunger disposed in the primary chamber and defining a storage chamber, and a valve for selectively providing fluid communication between the storage chamber and the primary chamber. The preloaded fluid may be pressurized and may comprise, for example, a gas (other than air), a liquid, or a fluid containing a drug. The inflation device is preferably preloaded by the manufacturer and/or packager of the inflation device.

20 Claims, 3 Drawing Sheets

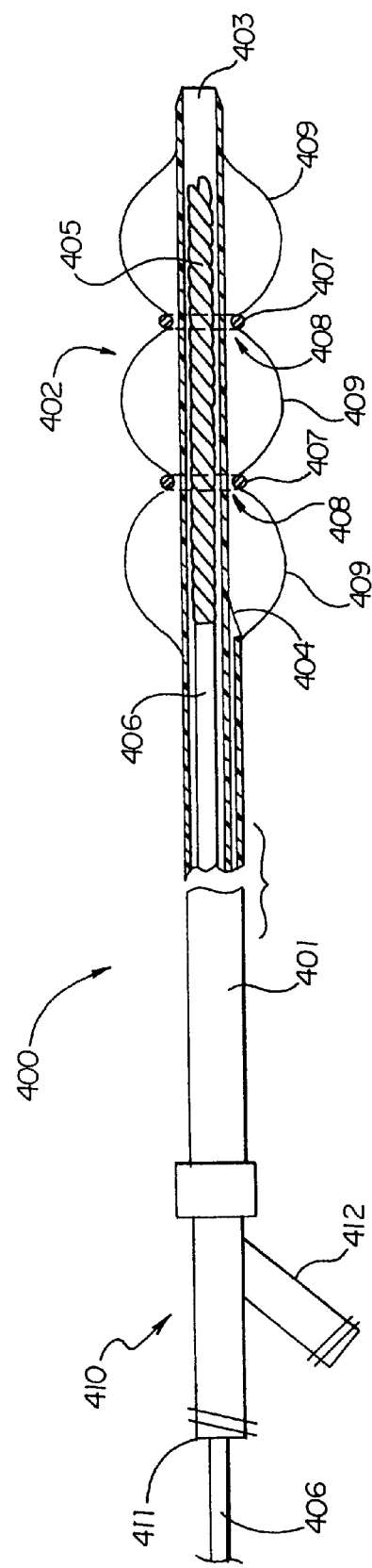

INFLATION DEVICE WITH STORAGE CHAMBER

RELATED APPLICATIONS

This application is related to patent application Ser. No. 09/644,754, filed Aug. 23, 2000 now U.S. Pat. No. 6,471,671 entitled PRELOADED GAS INFLATION DEVICE FOR BALLOON CATHETER, the entire disclosure of which is hereby incorporated by reference.

FIELD OF THE INVENTION

The present invention generally relates to inflation devices. More specifically, the present invention relates to inflation devices such as syringes used to inflate and deflate balloon catheters.

BACKGROUND OF THE INVENTION

Balloon catheters are sometimes inflated with gas, rather than liquid, because the balloon can be inflated and deflated more quickly than a comparable volume of saline or other liquid inflation media. Gas inflation has proved particularly useful in inflation of balloon centering catheters used in radiation therapy, which relies on a centering balloon to prevent the radiation source from being too close to one side of the target vessel. The use of gas rather than liquid decreases the amount of attenuation of radiation between the radiation source and the vessel wall.

While gas filled balloons are advantageous in some situations, the prior art process of preparing an inflation device for gas inflation is much more complicated than that for liquid inflation. Although air would be relatively easy to load into an inflation device, air is not a suitable inflation medium, because air does not rapidly dissolve in blood. In the event that the balloon bursts or leaks, bubbles could be formed in the arterial blood, impeding blood flow. In addition, a chief component of air, nitrogen, is not desirable for balloon inflation because nitrogen gas has thrombogenic properties which may present clinical risks in the event that the balloon bursts. Accordingly, it is desirable to use a gas other than air and to prevent air contamination of the gas used. A preferable gas used for balloon inflation is carbon dioxide.

Many medical facilities have built-in plumbing systems that provide gases such as carbon dioxide. Alternatively, a pressurized gas canister of carbon dioxide may be used. In either case, the pressurized source of carbon dioxide must be connected to a reduction valve to fill the inflation device with gas. The reduction valve lowers the pressure of the gas to a pressure suitable for the syringe. The reduction valve may utilize several stopcocks that must be opened for the gas to flow. For example, a first stopcock may be located at the reduction valve, a second stopcock may be located at the catheter connection point, and a third stopcock may be located at the syringe. Such systems are physically cumbersome and unwieldy, and require considerable preparation time by skilled medical personnel. Accordingly, a desirable feature in an inflation device would be an inflation syringe preloaded with a specified gas which the physician could conveniently use without extensive preparation and equipment.

Unfortunately, however, the storage of gas in a syringe mechanism presents several difficulties. Most plastics used in syringe manufacture are gas-permeable, at least to some extent. In addition, most stopcocks and syringe plungers, even when manufactured to precise specifications, are subject to leakage over extended periods of storage. Finally, packaging materials used to maintain sterility are usually gas permeable to facilitate ETO sterilization. These factors contribute to loss of the stored gas and/or contamination of the stored gas by air.

SUMMARY OF THE INVENTION

To address these problems, related U.S. patent application Ser. No. 09/644,754, filed Aug. 23, 2000 entitled PRELOADED GAS INFLATION DEVICE FOR BALLOON CATHETER discloses a number of different inflation devices preloaded with an inflation gas (other than air). Such inflation devices generally include a barrel defining a chamber preloaded with the inflation gas, and include some means for preventing air contamination of the inflation gas.

To further address these problems, the present invention provides several embodiments of an alternative inflation device. The present invention generally provides inflation devices that are preloaded with a fluid (e.g., a gas other than air) stored in a chamber in the plunger. By utilizing a storage chamber defined by the plunger, the present invention makes use of space that is otherwise underutilized and may be more readily protected against contamination.

For example, an inflation device in accordance with one embodiment of the present invention includes a barrel defining a primary chamber therein, a plunger disposed in the primary chamber and defining a storage chamber, and a valve for selectively providing fluid communication between the storage chamber and the primary chamber. The preloaded fluid may be pressurized and may comprise, for example, a gas (other than air), a liquid, or a fluid containing a drug. The inflation device is preferably preloaded by the manufacturer and/or packager of the inflation device.

The inflation devices of the present invention are suitable for inflating and deflating a wide variety of balloon catheters such as a centering balloon catheter or an angioplasty balloon catheter. The inflation device of the present invention is particularly useful in a medical system for intravascular delivery of ionizing radiation using a centering balloon catheter. In addition, although described with specific reference to a syringe type inflation device for purposes of illustration, other closed volume inflation devices are within the scope of the present invention.

BRIEF DESCRIPTION OF THE DRAWINGS

FIG. 5 is a partially cross-sectioned side view of a balloon catheter suitable for use in combination with the inflation device illustrated in FIG. 1.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
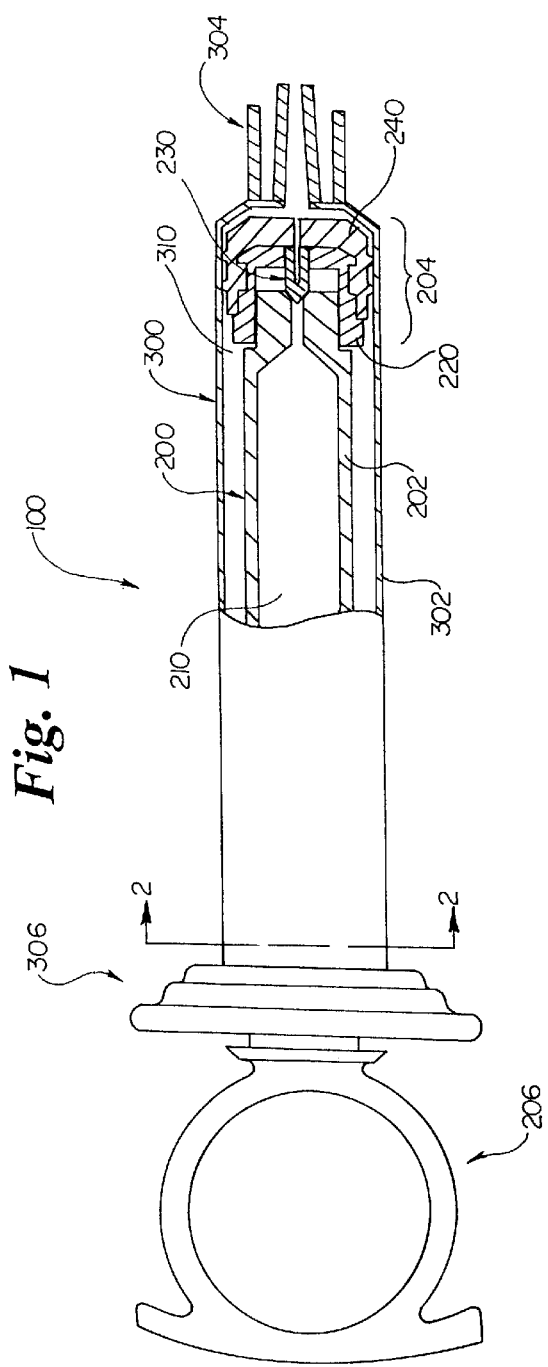
FIG. 1 is a partially cross-sectioned plan view of an inflation device in accordance with an embodiment of the present invention.

Refer now to FIG. 1 which illustrates a partially cross-sectioned plan view of an inflation device 100 in accordance with an embodiment of the present invention. The inflation device 100 includes a plunger 200 slidably disposed in a barrel 300.

The barrel 300 includes a body portion 302 having a proximal end and a distal end. A connector 304 (e.g., a male Luer fitting as shown) is provided at the distal end of the barrel body 302 to facilitate fluid connection to a balloon catheter, such as the centering balloon catheter 400 illustrated in FIG. 5. A handle or gripping surface 306 is provided at the proximal end of the barrel body 302. The barrel body 302 defines a primary chamber 310 in which the plunger 200 is disposed. The body portion 302 of the barrel 300 may be made of conventional syringe materials including glass, polycarbonate, acrylic, and/or polyethylene terephthalate.

The plunger 200 includes a shaft 202 having a proximal end and a distal end. A seal assembly 204 is connected to the distal end of the shaft 202. A handle 206 is connected to the proximal end of the shaft 202. The shaft 202 of the plunger 200 defines a storage chamber 210. Storage chamber 210 may contain a fluid such as a gas (other than air) or a liquid. A preferred fluid for use in intravascular radiation treatment is $CO_2$ gas.

The fluid contained in the storage chamber 210 is preferably pressurized (i.e. above ambient pressure) and preferably preloaded by the manufacturer or packager of the inflation device 100. Preferably, the chamber 210 contains a sufficient amount of fluid to fill the barrel 300. For example, if the volume of the barrel 300 is approximately 10 cc, the chamber 210 of the plunger 200 preferably contains a sufficient amount of pressurized fluid to approximate 10 cc of fluid at ambient pressure. Those skilled in the art will recognize that the size of the chamber 210 may be adjusted depending upon the size of the barrel 300, the compressibility of the stored fluid, and the storage pressure in the chamber 210.

The shaft 202 defining the chamber 210 preferably comprises a material which is both durable and relatively impermeable to fluids (gas and/or liquid) to facilitate long term storage (e.g., shelf life of six or more months) without substantial pressure loss or contamination. For example, particularly for the storage of a gas, the shaft 202 defining the storage chamber 210 may comprise a material having low gas permeability such as a metal (e.g., stainless steel, aluminum) or a polycarbon based material (e.g., polycarbonate), including coatings, laminates, composites, etc thereof.

The seal assembly 204 of the plunger 200 provides a movable and fluid tight seal with the inside surface of the barrel body 302 to affect changes in the internal volume of the primary chamber 310 upon longitudinal actuation of the plunger 200 relative to the barrel 300. The seal assembly 204 includes a body portion 220, a valve 230 and a gasket 240, as will be described in greater detail with reference to FIG. 3.

The valve 230 may comprise a needle valve as shown or other valve types known to those skilled in the relevant art. The valve 230 may be formed of a durable and low permeability material as described with reference to the plunger shaft 202. The valve 230 permits selective fluid communication between the storage chamber 210 in the plunger 200 and the primary chamber 310 in the barrel 300. The valve 230 may be selectively opened and closed by relative rotation between the plunger shaft 202 and the seal assembly 204.

Figure 2:
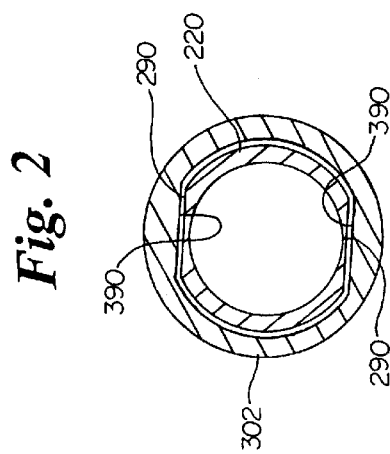
FIG. 2 is a cross-sectional view taken along line 2—2 in FIG. 1, showing the plunger in the retracted position.

Relative rotation between the shaft 202 and the seal assembly 204 may be accomplished utilizing a mating surface 290 of the seal body 220 and a mating surface of the barrel body 302. As best seen in FIG. 2, which shows the plunger 200 retracted in the proximal direction relative to the barrel 300, the keyed surfaces 290 of the seal body 220 engage and mate with the keyed surfaces 390 of the barrel body 302 to limit relative rotation therebetween. The shaft 202 of the plunger 200 has a smaller diameter than the keyed portion 390 of the barrel 300 such that rotation therebetween is not limited. Thus, by retracting the plunger 200 in the proximal direction relative to the barrel 300, the keyed surfaces 290/390 engage to limit relative rotation therebetween. By rotating the plunger handle 206 and plunger shaft 202 relative to the barrel 300, the valve 230 may be selectively opened and closed depending on the direction of rotation. Those skilled in the art will recognize that the keyed surfaces 290/390 may be replaced by other mating surfaces to limit relative rotation therebetween.

To facilitate discussion of a preferred method use of the inflation device 100, it is useful to first discuss an example of a balloon catheter suitable for use in combination with the inflation device 100. FIG. 5 illustrates a partially cross-sectioned side view of a centering balloon catheter 400 for use in delivering and centering a radioactive radiation source in the vasculature of a patient. The balloon catheter 400 is substantially disclosed in U.S. Pat. No. 5,976,106 to Verin et al., the entire disclosure of which is hereby incorporated by reference.

The centering balloon catheter 400 includes an elongate shaft 401 and a distally mounted balloon 402. The proximal and distal ends of the balloon 402 are adhesively secured to the elongate shaft 401 as is conventional in the art. The elongate shaft 401 includes a combined purpose guidewire/radiation source wire lumen 403 which is adapted to accept a conventional guidewire and/or a radioactive source wire 406 having a distally disposed radiation emitter 405. The elongate shaft 401 also includes an inflation lumen 404 which is in fluid communication with the interior of the balloon 402 to facilitate inflation and deflation thereof.

To facilitate centering in a curved vessel, the balloon 402 includes a plurality of constrictions 407 defining a plurality of balloon lobes 409. Fluid communication between each of the lobes 409 is accomplished by way of small passages 408. The constricted portions 407 may comprise, for example, belt means which restrict inflation of the balloon 402, but leave sufficient space 408 to provide fluid communication between the lobes 409.

A manifold 410 is connected to the proximal end of the elongate shaft 401. The manifold 410 includes a guidewire and radiation source wire arm 411 to facilitate insertion of a guidewire and to facilitate connection to an afterloader (not shown). The manifold 410 also includes an inflation arm 412 to facilitate connection to an inflation device, such as inflation device 100. Specifically, the connector 304 of the inflation device 100 may be connected to the inflation arm 412 of the manifold 410 to fluidly connect the primary chamber 310 of the inflation device 100 to the inflation lumen 404 and interior of the balloon 402. The inflation device 100 may thus be used to selectively inflate and deflate the balloon 402, as will be described in greater detail hereinafter.

In use, the inflation device 100 is removed from the packaging (not shown) with the storage chamber 210 containing the desired pressurized fluid. The plunger 200 is retracted in the proximal direction relative to the barrel 300 to engage the keyed surfaces 290/390. The plunger shaft 202 is manually rotated relative to the barrel body 302 by the physician utilizing handles 206/306. Upon rotation of the plunger shaft 202, the valve 230 is opened by virtue of a threaded connection discussed in more detail hereinafter, thus releasing the pressurized fluid from the storage chamber 210 into the primary chamber 310. The valve 230 is then closed by manually rotating the plunger shaft 202 relative to the barrel 300 in the opposite direction utilizing handles 206/306. The plunger 200 is then advanced in the distal direction until the desired volume of fluid is contained in the primary chamber 310 of the barrel 300. A balloon catheter such as centering balloon catheter 400 is then connected to the connector 304 to provide fluid communication between the inflation lumen 404 and the primary chamber 310. The balloon 402 may then be selectively inflated and deflated by longitudinal actuation of the plunger 200 relative to the barrel 300.

Figure 3:
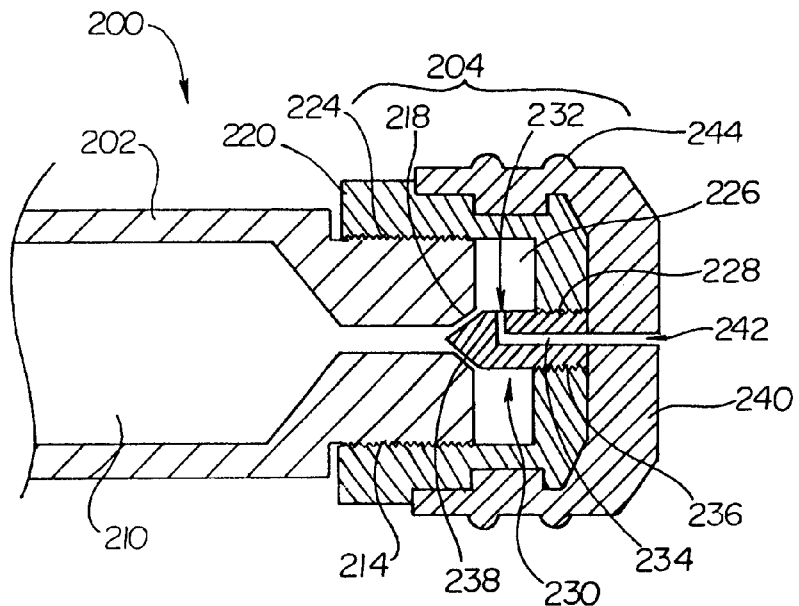
FIG. 3 is a detailed longitudinal cross-sectional view of the distal end of the plunger illustrated in FIG. 1.

Refer now to FIG. 3 which illustrates a longitudinal cross-sectional view of the distal end of the plunger 200, particularly providing a detailed view of the seal assembly 204. The seal assembly 204 includes a body portion 220 having internal threads 224 which engage external threads 214 carried by the distal end of the plunger body 202. The body portion 220 also has internal threads 228 which engage external threads 236 carried by the valve 230. The body portion 220 defines an internal volume 226 which is in fluid communication with the storage chamber 210 of the plunger body 202 by way of plunger lumen 212 when the valve 230 is in the open position as illustrated.

Valve 230 includes a valve port 232 and a valve lumen 234 which are in fluid communication with the internal volume 226 defined between the seal body 220 and the distal end of the plunger shaft 202. The valve lumen 234 is in fluid communication with the gasket lumen 242 such that fluid communication is established between the internal volume 226 and the primary chamber 310 of the barrel 300. The valve 230 includes a valve surface 238 which establishes a fluid tight seal with the valve seat 218 defined by the distal end of the plunger shaft 202. The valve surface 238 may be selectively engaged and disengaged from the valve seat 218 by rotation of the seal body 220 relative to the plunger shaft 202 as described previously. By virtue of the threaded connection 214/224, rotation of the body portion 220 relative to the plunger 202 causes longitudinal displacement therebetween and thereby causes the valve surface 238 to selectively engage and disengage the valve seat 218. Specifically, relative rotation between the plunger shaft 202 and the seal body 220 causes relative rotation between the threads 214/224 which in turn cause longitudinal displacement between the plunger shaft 202 and the seal assembly 204 thereby opening or closing the valve 230, depending on the direction of rotation. By opening the valve 230, fluid communication is established between the storage chamber 210 and the primary chamber 310 by way of lumen 212, internal volume 226, valve port 232, valve lumen 234 and gasket lumen 242.

Figure 4:
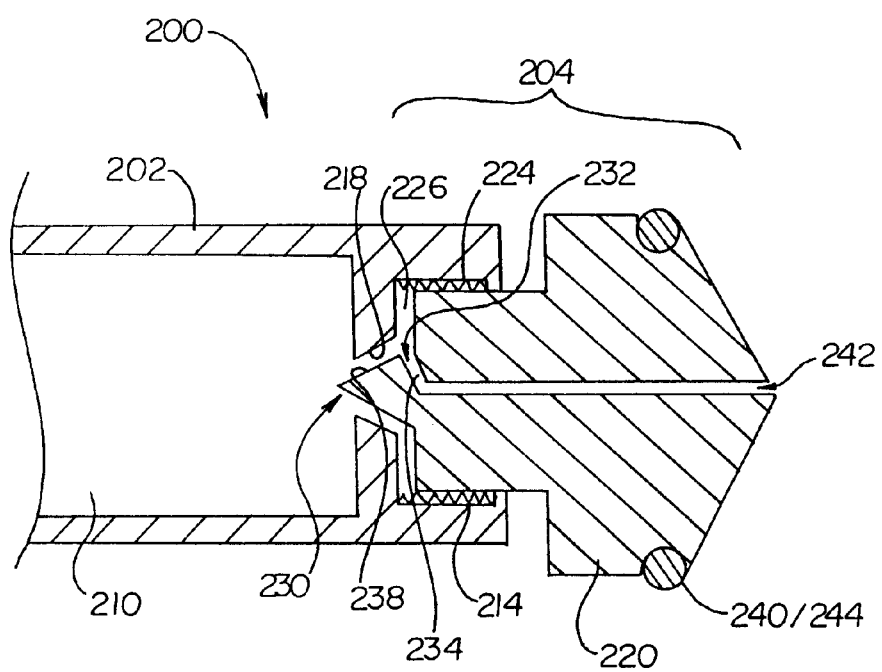
FIG. 4 is a detailed longitudinal cross-sectional view of an alternative embodiment of the distal end of the plunger illustrated in FIG. 1.

The gasket 240 includes one or more rubber o-rings 224 to provide a fluid tight seal with the inside surface of the barrel body 302. Alternatively, the rubber gasket 240 may simply comprise a rubber o-ring 244 which may be snap-fit into a recess defined in the body portion 220 as shown in FIG. 4, which illustrates an alternative embodiment of the distal portion of the plunger 200. In this embodiment, the body portion 220 is integrally formed with the valve 230. This particular embodiment is adventitious because the design has been simplified from a manufacturing stand point by reducing the number of parts and simplifying the gasket geometry 240/224. The function and use of this alternative embodiment is otherwise substantially the same as described with reference to FIG. 3.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An inflation device for selectively inflating and deflating a balloon of a balloon catheter, the inflation device comprising:
   a barrel defining a primary chamber therein, the barrel having a connector for fluid connection to the balloon catheter;
   a plunger disposed in the primary chamber, the plunger defining a storage chamber; and
   a valve for selectively providing fluid communication between the storage chamber and the primary chamber.

2. An inflation device as in claim 1, wherein the storage chamber contains a pre-loaded pressurized fluid.

3. An inflation device as in claim 2, wherein the fluid comprises a gas.

4. An inflation device as in claim 2, wherein the fluid comprises a liquid.

5. An inflation device as in claim 2, wherein the fluid contains a drug.

6. An inflation device as in claim 1, wherein the plunger includes a shaft and a seal, and wherein the shaft of the plunger defines the storage chamber.

7. An inflation device as in claim 6, wherein the valve is actuated by relative rotation between the seal and the shaft of the plunger.

8. An inflation device as in claim 7, wherein a keyed portion of the barrel mates with a keyed portion of the seal to limit relative rotation therebetween.

9. An inflation device as in claim 8, wherein the keyed portion of the barrel does not mate with the shaft of the plunger to permit relative rotation therebetween.

10. An inflation device as in claim 9, wherein the keyed portion of the barrel is disposed at a proximal end thereof.

11. An inflation device as in claim 8, wherein the seal includes a body portion and a gasket.

12. An inflation device as in claim 11, wherein the body portion of the seal is connected to the valve.

13. An inflation device as in claim 12, wherein the body portion of the seal is integral with the valve.

14. An inflation device as in claim 12, wherein the body portion of the seal defines a lumen in fluid communication with the primary chamber of the barrel.

15. An inflation device as in claim 6, wherein the shaft of the plunger defining the storage chamber includes a metal to reduce gas permeability.

16. An inflation device as in claim 15, wherein the metal comprises a coating.

17. An inflation device as in claim 15, wherein the metal comprises a laminate.

18. An inflation device as in claim 6, wherein the shaft of the plunger defining the storage chamber includes polycarbon to reduce gas permeability.

19. An inflation device as in claim 6, wherein the valve includes a metal to reduce gas permeability.

20. An inflation device as in claim 6, wherein the valve includes polycarbon to reduce gas permeability.

* * * * *